United States Patent [19]

Sandler et al.

[11] Patent Number: 5,166,431
[45] Date of Patent: * Nov. 24, 1992

[54] PREPARATION OF ALKANESULFONAMIDES

[75] Inventors: Stanley R. Sandler; James S. Perilli, both of Springfield; John F. Kennoy, Horsham, all of Pa.

[73] Assignee: Elf Atochem North America, Inc., Philadelphia, Pa.

[*] Notice: The portion of the term of this patent subsequent to Nov. 13, 2007 has been disclaimed.

[21] Appl. No.: 718,136

[22] Filed: Jun. 20, 1991

Related U.S. Application Data

[63] Continuation-in-part of Ser. No. 584,830, Sep. 19, 1990, abandoned, which is a continuation-in-part of Ser. No. 277,824, Nov. 30, 1988, Pat. No. 4,970,339.

[51] Int. Cl.[5] ................. C07C 303/38; C07C 303/44
[52] U.S. Cl. ........................................ 564/98; 564/96
[58] Field of Search ..................... 564/46, 98

[56] References Cited

U.S. PATENT DOCUMENTS

| 3,300,529 | 1/1967 | Berkelhammer et al. | 564/97 |
| 3,336,383 | 8/1967 | Linden et al. | 260/556 |
| 3,781,441 | 12/1973 | Collins | 514/603 |
| 4,260,497 | 4/1981 | Bauman | 252/8.75 |
| 4,710,581 | 12/1987 | Stahly et al. | 560/20 |

FOREIGN PATENT DOCUMENTS

| 0466527 | 7/1950 | Canada . |
| 0276182 | 7/1988 | European Pat. Off. . |
| 2002460 | 7/1970 | Fed. Rep. of Germany . |
| 2201578 | 10/1972 | Fed. Rep. of Germany . |

Primary Examiner—Richard L. Raymond
Assistant Examiner—Peter G. O'Sullivan
Attorney, Agent, or Firm—Royal E. Bright

[57] ABSTRACT

A method for the preparation of alkanesulfonamides in high purity and high yield using solvents selected from $C_3$ to $C_8$ cyclic ethers or mixtures thereof is disclosed. The final products have use as synthetic intermediates for the manufacture of useful final products.

30 Claims, No Drawings

PREPARATION OF ALKANESULFONAMIDES

CROSS REFERENCE TO COPENDING APPLICATIONS

This application is a continuation-in-part of U.S. application Ser. No. 07/584,830 filed Sep. 19, 1990, now abandoned, which is a continuation-in-part of U.S. application Ser. No. 07/277,824 filed Nov. 30, 1988, now U.S. Pat. No. 4,970,339.

BACKGROUND OF THE INVENTION

This invention relates to alkanesulfonamides and more particularly to a novel process for their preparation.

Synthetic methods for organosulfonamides in general and for alkanesulfonamides in particular are well known in the literature. Many of these involve treating the corresponding sulfonyl chloride with ammonia or a primary or secondary amine in the presence of various organic solvents. These prior art processes all provide an initially crude product which is contaminated with by-products and requires further purification before it can be used further.

The present invention provides a method for the synthesis of alkanesulfonamides which provides a number of advantages over previously reported procedures.

The present invention contemplates a direct synthesis of alkanesulfonamides from readily available starting materials. The sulfonamides recovered from the crude reaction mixture are sufficiently pure for use as synthetic intermediates without further treatment.

European Patent application 0276182 describes the preparation of $C_1$–$C_4$ alkanesulfonamides using di- or mono- alkoxy alkane solvents. No equivalence to other solvents is suggested.

U.S. Pat. No. 3,300,529 describes a process for preparing N-alkyl and N,N-dialkyl-substituted ethylenesulfonamides by simultaneous dehydrochlorination and amination of $\beta$-chloro-alkanesulfonylchlorides in any unreactive solvent. Included in the general list of suitable solvents are tetrahydrofuran and "ether solvents" in general. No particular advantage for any particular solvent in the reaction at issue is pointed out. The use of any of the solvents in the preparation of saturated alkanesulfonamides is not discussed.

U.S. Pat. No. 3,781,441 describes a process for making 4-chloro-3,5-dinitrobenzenesulfonamide from the corresponding sulfonyl chloride by reaction with ammonia in various solvents at temperatures below 10° C. Included among the list of suitable solvents are $C_4$-$C_8$ cyclic ethers. Tetrahydrofuran is specifically mentioned. Here the process of the patent is concerned with avoiding displacement of the aryl chlorine by ammonia. No particular advantage to the use of cyclic ethers such as tetrahydrofuran over any of the other listed solvents is stated.

U.S. Pat. No. 3,574,740 describes the preparation of methanesulfonamide and its derivatives by treating methanesulfonyl chloride in a $C_1$ to $C_4$ nitroalkane with ammonia or a primary or secondary amine. Substitution of other solvents is not suggested. As stated in this patent, the solubility of methanesulfonamide in nitroalkanes is highly temperature dependent, requiring that filtration to remove by-product be conducted at elevated temperature. In addition, processing in nitroalkanes produces discolored products. More complex processing is required by the necessity of conducting hot filtrations and removing undesired color from the product.

Czechoslovakia Patent 235,626 describes treatment of methanesulfonyl chloride in solution in toluene with gaseous ammonia followed by crystallization of the methanesulfonamide product from a toluene/ethanol mixture after concentration. Ammonium chloride is soluble in the toluene/ethanol reaction mixture described in the patent to over 1% by weight concentration. The product must be isolated by crystallization from the concentrated reaction mixture to separate it from the ammonium chloride remaining in solution. This results in a drop in yield to about 90%. On a large scale, this small drop in yield can have significant economic consequences. No other solvents are suggested as equivalents or as alternatives.

J. Am. Chem. Soc., Vol. 75, page 934 (1953), J. Am. Chem. Soc., Vol. 77, page 170 (1955), Monatsh., Vol. 89, page 285 (1958) as summarized in Chem Abstracts Vol. 53, Col. 1140i (1959) and J. Chem. Soc., Vol. 125, page 1463 (1924) all describe treatment of methanesulfonyl chloride in benzene with anhydrous ammonia to give the desired methanesulfonamide. No other solvents are suggested as suitable equivalents or alternatives.

Zhur. Obschei Khim., Vol 18, page 729 (1948) as summarized in Chem. Abstracts Vol. 43, Col. 120f describes treatment of methanesulfonyl chloride in dry diethyl ether with anhydrous ammonia followed by evaporation of solvent and extraction of the residue with benzene to obtain the methanesulfonamide product. Once again, other solvents are not suggested as suitable equivalents or alternatives.

Benzene is a known carcinogen and, while it can be handled industrially, its use complicates any process in which it is employed.

None of the teachings of these prior art references suggest to one of skill in the art of organic chemistry that an alkanesulfonyl chloride may be dissolved in the solvents comprehended by the instant invention and treated with anhydrous ammonia or with primary or secondary amines with the result that a substantially complete separation of ammonium chloride or amine hydrochloride is obtained from the desired alkanesulfonamide which may then be recovered in high purity and in extremely high yields (93% and greater) simply by evaporation of solvent.

SUMMARY OF THE INVENTION

The invention provides a process for the preparation of alkanesulfonamides having the formula:

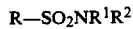

wherein R is selected from methyl or ethyl; and $R_1$ and $R^2$ may be the same or different and are selected from hydrogen or methyl which comprises treating an alkanesulfonyl halide having the formula:

wherein R is as defined hereinabove and X is fluorine, chlorine, bromine or iodine with an effective amount of a compound of the formula:

wherein $R^1$ and $R^2$ are as defined hereinabove in the presence of a solvent selected from saturated $C_3$ to $C_8$ cyclic ethers or mixtures thereof; with the proviso that when the solvent is tetrahydrofuran and R is methyl, $R^1$ and $R^2$ are not both hydrogen.

Special mention is made of a process wherein, additionally, after treatment of the alkanesulfonyl halide is complete, excess compound of the formula $HNR^1R^2$ is removed from the treatment mixture.

Special mention is also made of a process wherein the alkanesulfonyl halide is an alkanesulfonyl chloride.

Special mention is also made of a process wherein the compound of the formula $HNR^1R^2$ is ammonia.

Special mention is also made of a process wherein, additionally, the alkanesulfonamide product is recovered by separation of substantially all by-product ammonium chloride, or primary or secondary amine hydrochloride from the treatment mixture and subsequent removal of solvent.

Special mention is also made of a process wherein the $C_3$–$C_8$ cyclic ether is tetrahydrofuran.

Special mention is also made of processes wherein the alkanesulfonyl chloride is methanesulfonyl chloride.

The tangible embodiments produced by the processes of the invention are known materials which have utility as synthetic intermediates in the manufacture of agricultural chemicals and chemicals useful in the treatment of textiles and paper.

The product compounds are crystalline, waxy materials or liquids whose identity is positively confirmed by physical constants such as melting points and nuclear magnetic resonance spectral analysis and whose purity is positively confirmed by a standard functional group analysis test for the sulfonamide group.

DETAILED DESCRIPTION OF THE INVENTION

According to the process of the invention, alkane-sulfonamides may be prepared in batch, semi-continuous or continuous fashion.

An alkanesulfonyl chloride, for example methane-sulfonyl chloride may be contacted with an effective amount of ammonia or amine in a cyclic ether solution, for example tetrahydrofuran, conveniently at about atmospheric or super- atmospheric pressure. Cooling may be necessary to maintain the desired temperature because the reaction is normally exothermic. The reaction is normally rapid and is usually complete by the time the addition of reagents to the contact or treatment zone is completed. Preferably, excess ammonia or amine may then be vented from the reaction mixture and by-product ammonium chloride or amine hydrochloride which precipitates out of the reaction mixture may then be separated by standard means, such as filtration, or centrifugation. The alkanesulfonamide, for example methanesulfonamide, may be recovered conveniently by evaporation of the solvent from the organic phase to leave the product as a high purity residue.

Depending on the temperature at the end of solvent evaporation, the alkanesulfonamide may be in solid or molten form or a liquid. If molten, it may be used directly in further processing without solidification or it may be fed to a conventional flaker or other known conventional solidification means to provide solid product. The product whether in molten, solid or liquid form is substantially pure when recovered.

The methane and ethanesulfonyl chloride starting materials are commercially available, as are ammonia and mono- and dimethylamine. It will be obvious to one of skill in the art to select a purity grade of starting materials that will provide the desired degree of purity of the final product.

The order of addition of reactants is not particularly critical for most reaction conditions, but it is preferred to add the lower alkanesulfonyl halide to a solution of ammonia or amine in the solvent to obtain the highest purity product. It has been found that some methanesulfonimide is formed if ammonia is added to a methanesulfonyl chloride solution in tetrahydrofuran at temperatures in the vicinity of 66° C. The rate of addition is also not especially critical, but, as the reaction is exothermic, it can conveniently be performed at a rate at which the available cooling capacity will be adequate to maintain the desired temperature. The reaction or treatment time is also not critical and normally the reaction will be complete after complete addition of all reactants in a batch reaction. In a continuous or semicontinuous reaction, one of skill in the art will be able to control the relative feed rate of the reactants into the treatment or contact zone and the rate of flow through and out of that zone so that the reaction is essentially complete in the treatment zone by employing standard monitoring techniques well known in the art.

Although the process of the invention has been specifically illustrated herein by reference to alkanesulfonyl chlorides and to ammonia, one of skill in the art will recognize that other alkanesulfonyl halides such as alkanesulfonyl fluorides, bromides and iodides may be substituted for the specifically illustrated chlorides and will be full equivalents thereto and that N-methyl and N,N-dimethyl amines may be substituted for ammonia and will be full equivalents thereto.

Although the process of the invention has been illustrated herein by the use of a reaction performed at about room temperature (about 20°–25° C.), the temperature range of the reaction is also not especially critical and can vary over a wide range from about −20° C. to about 150° C. Preferably it may range from about 10° C. to about 70° C.

One of skill in the art will recognize that due to the volatility of tetrahydrofuran and more particularly of ammonia and of the primary and secondary amines, if the reaction is run in the higher portion of the suitable temperature range, it may be necessary to employ super-atmospheric pressure to avoid excessive losses of materials from the reaction or treatment zone.

One of skill in the art will also understand that an effective amount of ammonia and of the primary and secondary amines to be employed in the treatment or reaction will be at least the two molar stoichiometric equivalent amount and will preferably be a slight excess over that amount. The exact amount of the excess is not critical. A 10% to 50% excess has been found sufficient but lesser amounts may be employed. Larger amounts may also be employed but provide no apparent advantage. Excess ammonia may of course be recovered from the final reaction mixture by known conventional means such as purging from the reaction mixture and compression and/or condensation back to a liquid.

Removal of excess ammonia and of excess amines from the reaction mixture prior to separation of by-product ammonium chloride or amine hydrochloride is preferred because it has been found to provide more complete separation of ammonium chloride and of amine hydrochloride from the final product. If traces of ammonium chloride or amine hydrochloride are not objectionable in the final product, then it is unnecessary to remove excess ammonia or amine.

Excess of volatile primary and secondary amines may be removed in a fashion similar to removal of excess ammonia. In the event such amines are insufficiently volatile, the excess may be treated with a stoichiometric equivalent of mineral acid such as hydrochloric acid. The resulting salt will, of course, be separable with the amine salt produced as a by-product of the original reaction.

As used herein and in the appended claims, the term "alkanesulfonyl halide" contemplates a compound of the formula $RSO_2X$ and the term "alkanesulfonamide" contemplates a compound of the formula $RSO_2NR^1R^2$ wherein X is fluorine, chlorine, bromine or iodine and wherein R, $R^1$ and $R^2$ are as defined hereinabove.

One of skill in the art will also recognize that although the invention has been specifically illustrated in the specification by the use of tetrahydrofuran, the invention comprehends as full equivalents other saturated cyclic ethers such as alkyl substituted tetrahydrofurans, for example methyl or ethyl tetrahydrofuran, 1,4-dioxane and 1,3-dioxolane, as well as mixtures of such cyclic ethers.

The following examples further illustrate the best mode contemplated by the inventors for the practice of their invention.

EXAMPLE 1

A solution of methanesulfonyl chloride (120.0 g, 1.05 moles) in tetrahydrofuran (434.0 g) was cooled to 0° C. To the cooled solution while stirring and maintaining the temperature within a range of from 2° to 7° C. was added anhydrous ammonia (53.0 g, 3.1 moles) as a gas over a period of 2.5 hours. The reaction mixture was then warmed to room temperature (about 25° C.) and excess ammonia vented. The remaining reaction mixture was then filtered and the filter cake comprising ammonium chloride was washed with additional tetrahydrofuran (2×100 ml). The filtrate and washings were combined and the tetrahydrofuran evaporated under reduced pressure to give methanesulfonamide (92.3 g, 93.0% yield), m.p. 86°–90° C. Analysis: (% by weight) 99.0% $CH_3SO_2NH_2$, 0.17% $NH_4Cl$.

EXAMPLE 2

Gaseous ammonia (38.0 g, 2.2 moles) was added over a period of 1.75 hr. to tetrahydrofuran (439.0 g, 500 ml) at −22° C. While stirring, methanesulfonyl chloride (75.5 g, 51.0 ml, 0.65 mole) was added over a period of 20 minutes while the temperature of the mixture rose from −22° C. to +5° C. The reaction mixture was then allowed to warm to room temperature while excess ammonia was vented. Ammonium chloride (34.7 g, 100% yield) was removed from the reaction mixture by filtration and washing with fresh portions of tetrahydrofuran (3×50 ml). The filtrate and washings were combined and tetrahydrofuran evaporated under reduced pressure to yield methanesulfonamide (57.1 g, 99.4% yield) m.p. 86°–91° C. Analysis: 100% $CH_3SO_2NH_2$, 0.1% $NH_4Cl$.

EXAMPLE 3

Tetrahydrofuran (6,061 g) was cooled to about 10° C. while ammonia gas (55.0 g, 3.2 moles) was added over a period of nine minutes. Methanesulfonyl chloride (1482.3 g, 12.9 moles) and ammonia gas (639 g, 37.6 moles) were then added simultaneously over a period of four hours while stirring and maintaining the reaction mixture temperature at between 10° C. and 22° C. Excess ammonia gas was then vented. Ammonium chloride (674.5 g, 97.5% yield) was then separated by filtration and washed with fresh tetrahydrofuran (2×1 liter). Tetrahydrofuran was then evaporated from the combined filtrate and washings to give methanesulfonamide (1186.0 g, 96.7% yield) m.p. 87°–91° C. Analysis: $CH_3SO_2NH_2$ 99.3%, 0.4% $NH_4Cl$.

EXAMPLE 4

Charge tetrahydrofuran (5700 lb, 2585 Kg.) and methanesulfonyl chloride (1742 lb, 790.2 Kg.) into a sealed, stirred-tank reactor. While mixing and maintaining the temperature at about 25°–65° C., add ammonia gas (755 lb, 342.5 Kg.) under positive pressure.

Reduce the positive pressure in the reactor while venting excess ammonia. Separate ammonium chloride by centrifugation or filtration and wash with several small portions of fresh tetrahydrofuran. Remove tetrahydrofuran from the combined organics under sufficient positive pressure to keep the pot temperature above the melting point of the methanesulfonamide product. Flake the molten product in conventional fashion.

EXAMPLES 5 THROUGH 11

Continuous Reactor

Apparatus

A continuous back-mixed reactor system was set up as follows:

The reactor consisted of a vertical glass pipe section fitted with top and bottom end-plates. The bottom end-plate was drilled to allow connection of a pipe to the suction-side of an open-impeller centrifugal pump. The top end-plate was drilled to allow separate feed lines for ammonia, solvent, and methanesulfonyl chloride (MSC), as well as a vent line.

The discharge of the pump was sent to an external cooler and then split into two streams: a product take-off stream, and a recirculation stream, which was returned to the reactor via the MSC feed line. The contents of the reactor were agitated by the high flowrate of the recirculation stream. The reactor temperature was controlled by adjusting the coolant flow to the exchanger.

Solvent was fed to the reactor as a liquid, entering above the surface of the reaction mixture. MSC was fed to the reactor as a liquid, and was mixed with the recirculating stream; the MSC/recirculation mixture entered below the surface of the reaction mixture. Ammonia was fed to the reactor as a gas, entering below the surface of the reaction mixture. The reactor pressure was controlled, venting excess gas to maintain system pressure.

The operating procedure was as follows:

1. Purge the reactor with nitrogen to exclude air. Charge enough solvent to the reactor to raise the liquid level to the desired volume.
2. Start the recirculation pump.
3. Begin feeding ammonia to the reactor at the desired feedrate. Set the pressure controller to maintain the reactor at the desired operating pressure.
4. Begin feeding the solvent and the MSC at the desired feedrates. Open the product take-off line, and adjust the take-off flow to maintain the desired liquid volume in the reactor.
5. Adjust the coolant flow to the external cooler to maintain the reactor at the desired temperature.

6. Filter the product slurry to remove the precipitated ammonium chloride by-product. Boil-off the solvent (under vacuum, if necessary), leaving methanesulfonamide as the molten or solid product.

The continuous reactor was generally operated with a liquid volume of approximately 275 ml., including the liquid in the recirculation loop. Reaction pressures ranged from atmospheric to 25 psig, which was the maximum allowable pressure with the particular equipment used.

Solvent and MSC flows were adjusted to provide mean residence times of 5–45 minutes. The ratio of MSC to solvent were adjusted to provide MSC/solvent ratios of 0.05 to 0.30. Higher ratios and shorter residence times were not tested due to limitations of the feed system.

Temperatures were maintained at 80°–154° F. (27°–68° C.). Lower temperatures were not tested due to coolant limitations, while higher temperatures were not achievable due to heat losses from the uninsulated reactor system.

The purity of the methanesulfonamide produced by the continuous reactor system at typical temperatures, pressures, residence times, and MSC/solvent ratios are given below:

| Ex. No. | Temp. (°F.) | Pressure (psig) | Residence Time (min.) | MSC/Solvent (wt./wt.) | Methanesulfonamide Purity (wt. %) |
|---|---|---|---|---|---|
| 5 | 91 | 20 | 22 | 0.20 | 98.8 |
| 6 | 89 | 20 | 15 | 0.13 | 98.9 |
| 7 | 89 | 5 | 22 | 0.14 | 97.2 |
| 8 | 118 | 20 | 15 | 0.21 | 98.4 |
| 9 | 90 | 5 | 15 | 0.21 | 97.8 |
| 10 | 115 | 5 | 23 | 0.15 | 100.0 |
| 11 | 154 | 21 | 8 | 0.30 | 99.8 |

EXAMPLE 12

Continuously meter tetrahydrofuran (500 lb./hr., 227 Kg./hr.) methanesulfonyl chloride (153 lb./hr., 69.4 Kg./hr.) and anhydrous ammonia (66 lb./hr., 30 Kg./hr.) under pressure through a cooled static mixer while maintaining the reaction zone temperature at about 25° to 65° C. Upon exiting the reactor, allow the mixture to flush and vent excess ammonia. Separate solid ammonium chloride which separates from the reaction mixture using a continuous sold/liquid separation system. Wash the recovered solids with fresh portions of tetrahydrofuran and combine the washings with the organic phase from the reaction mixture. Evaporate the tetrahydrofuran from the combined organics and recover the methanesulfonamide product as a hot melt which may be flaked for storage. Recover the tetrahydrofuran by condensation of the evaporated material and restabilize the condensation for reuse in conventional fashion. The solid ammonium chloride of high purity may also be dried in conventional fashion.

COMPARATIVE EXAMPLE

Determination of the Solubility of Sulfonamides and Amine Salts in Various Solvents 10 g of the selected solvent was placed into a 50 ml Erlenmeyer flask equipped with a magnetic stirring bar and rubber stopper. Then the alkanesulfonamide that was to be tested was added to the solvent, in increments of 0.1 g, until the saturation point was reached. All solubility tests were conducted at room temperature.

Following this procedure, the solubility of the various compounds tabulated in the solvents listed were as follows:

| | Solvent | | | | |
|---|---|---|---|---|---|
| Compound | THF | Diethyl Ether | 2-Methyl THF | 1,4-Dioxane | 1,3-Dioxolane |
| Alkanesulfonamide | | | | | |
| $CH_3SO_2N(H)(H)$ | 1.5 | <0.1 | 0.7 | 1.5 | 2.2 |
| $CH_3SO_2N(CH_3)(H)$ | >5.0 | <0.1 | >5.0 | >5.0 | >5.0 |
| $CH_3SO_2N(CH_3)(CH_3)$ | 1.8 | 0.3 | 2.0 | >4.0 | >4.0 |
| $CH_3SO_2N(C_2H_5)(H)$ | >10.0 | >10.0 | — | — | — |
| $CH_3SO_2N(C_2H_5)(C_2H_5)$ | >6.0 | >6.0 | — | — | — |

| Compound | Solvent | | | | |
|---|---|---|---|---|---|
| | THF | Diethyl Ether | 2-Methyl THF | 1,4-Dioxane | 1,3-Dioxolane |
| $CH_3SO_2N(nC_4H_9)(H)$ | >10.0 | >10.0 | — | — | — |
| $CH_3SO_2N(nC_4H_9)(nC_4H_9)$ | >10.0 | >10.0 | — | — | — |
| $CH_3CH_2SO_2N(H)(H)$ | >6.0 | <0.1 | >4.0 | >4.0 | >4.0 |
| $CH_3CH_2SO_2N(CH_3)(H)$ | >5.0 | <0.1 | >5.0 | >5.0 | >5.0 |
| $CH_3CH_2SO_2N(CH_3)(CH_3)$ | >5.0 | <0.1 | >5.0 | >5.0 | >5.6 |
| $CH_3CH_2CH_2SO_2N(H)(H)$ | >5.0 | >5.0 | — | — | — |
| $CH_3(CH_2)_3SO_2N(H)(H)$ | >5.0 | >5.0 | — | — | — |
| Amine Salts | | | | | |
| $NH_4^+Cl^-$ | <0.1 | <0.1 | <0.1 | <0.1 | <0.1 |
| $(CH_3)_2NH_2^+Cl^-$ | <0.1 | <0.1 | — | — | <0.1 |
| $CH_3NH_3^+Cl^-$ | <0.1 | <0.1 | — | — | <0.1 |
| $CH_3CH_2NH_3^+Cl^-$ | <0.1 | <0.1 | — | — | — |
| $(n-C_4H_9)_2NH_2^+Cl^-$ | <0.1 | <0.1 | — | — | — |
| $n-C_4H_9NH_3^+Cl^-$ | <0.1 | <0.1 | — | — | — |

This data clearly demonstrates the substantial lack of solubility of ammonium chloride and the various amine hydrochlorides in all solvents tested thereby permitting excellent separation of these salts from sulfonamides having significant solubility in those solvents. It also demonstrates the selectivity of solubility for the cyclic ether solvents compared with diethyl ether for methane and ethane sulfonamides having either no N substituents or 1 or 2 methyl N substituent(s).

We claim:

1. A process for the preparation of alkanesulfonamides having the formula:

$$R-SO_2NR^1R^2$$

wherein R is selected from methyl or ethyl and $R^1$ and $R^2$ may be the same or different and are selected from hydrogen or methyl which consists essentially of treating an alkanesulfonyl halide having the formula:

$$RSO_2X$$

wherein R is as defined hereinabove and X is fluorine, chlorine, bromine or iodine with an effective amount of a compound of the formula:

$$HNR^1R^2$$

wherein $R^1$ and $R^2$ are as defined hereinabove in the presence of a solvent selected from saturated $C_3$ to $C_8$ cyclic ethers or mixtures thereof, with the proviso that when the solvent is tetrahydrofuran and R is methyl, $R^1$ and $R^2$ are not both hydrogen and recovering the alkanesulfonamide product by separation of by-product compound $H_2N^+R^1R^2X^-$ and subsequent evaporation of solvent.

2. A process as defined in claim 1 wherein the alkanesulfonyl halide is an alkanesulfonyl chloride.

3. A process as defined in claim 1 wherein additionally after treatment of the alkanesulfonyl halide is complete, excess compound of the formula $HNR^1R^2$ is removed from the treatment mixture.

4. A process as defined in claim 1 wherein the compound $HNR^1R^2$ is ammonia.

5. A process as defined in claim 2 wherein the compound $HNR^1R^2$ is ammonia.

6. A process as defined in claim 5 wherein additionally after treatment of the lower alkanesulfonyl chloride with ammonia is complete, unreacted excess ammonia is removed from the treatment mixture.

7. A process as defined in claim 1 wherein the saturated $C_3$ to $C_8$ cyclic ether is selected from the group consisting of tetrahydrofuran, alkyl substituted tetrahydrofuran, 1,4-dioxane, 1,3-dioxolane and mixtures thereof.

8. A process as defined in claim 1 wherein the by-product compound $H_2N^+R^1R^2X^-$ is ammonium chloride.

9. The process of claim 1 wherein the lower alkanesulfonyl halide is methanesulfonyl chloride.

10. The process of claim 3 wherein the lower alkanesulfonyl halide is methanesulfonyl chloride.

11. A process as defined in claim 7 wherein the lower alkanesulfonyl halide is methanesulfonyl chloride.

12. A process as defined in claim 1 wherein the solvent comprises tetrahydrofuran.

13. A process as defined in claim 2 wherein the solvent comprises tetrahydrofuran.

14. A process as defined in claim 3 wherein the solvent comprises tetrahydrofuran.

15. A process as defined in claim 7 wherein the solvent comprises tetrahydrofuran.

16. A process as defined in claim 11 wherein the solvent comprises tetrahydrofuran.

17. A process as defined in claim 1 which is run as a batch process.

18. A process as defined in claim 1 which is run as a semi-continuous process.

19. A process as defined in claim 1 which is run as a continuous process.

20. A process as defined in claim 1 wherein the alkanesulfonamide is recovered in the molten state after substantially all solvent is evaporated.

21. A process as defined in claim 8 wherein substantially pure ammonium chloride is recovered substantially quantitatively from the treatment mixture.

22. A process as defined in claim 9 wherein the compound $HNR^1R^2$ is ammonia and the alkanesulfonamide prepared is methanesulfonamide.

23. A process as defined in claim 22 wherein additionally after treatment of the lower alkanesulfonyl chloride is complete, unreacted excess ammonia is removed from the reaction mixture.

24. A process as defined in claim 23 wherein additionally the methanesulfonamide product is recovered by separation of by-product ammonium chloride and subsequent evaporation of tetrahydrofuran.

25. A process as defined in claim 1 wherein the alkanesulfonamide product is N-methyl-methanesulfonamide.

26. A process as defined in claim 1 wherein the alkanesulfonamide product is N, N-dimethyl-methanesulfonamide.

27. A process as defined in claim 1 wherein the alkanesulfonamide product is ethanesulfonamide.

28. A process as defined in claim 1 wherein the alkanesulfonamide product is N-methyl-ethanesulfonamide.

29. A process as defined in claim 1 wherein the alkanesulfonamide product is N,N-dimethyl-ethanesulfonamide.

30. A process as defined in claim 1 wherein the solvent comprises 1,3-dioxolane.

* * * * *